United States Patent [19]

Guire

[11] Patent Number: 4,722,906
[45] Date of Patent: Feb. 2, 1988

[54] BINDING REAGENTS AND METHODS

[75] Inventor: Patrick E. Guire, Eden Prairie, Minn.

[73] Assignee: Bio-Metric Systems, Inc., Eden Prairie, Minn.

[21] Appl. No.: 428,074

[22] Filed: Sep. 29, 1982

[51] Int. Cl.$^4$ .................. G01N 33/543; G01N 33/566
[52] U.S. Cl. ..................... 436/501; 436/518;
436/529; 436/543; 436/547; 435/7; 435/174;
435/177; 530/389; 530/810; 530/813
[58] Field of Search ............ 435/4, 7, 188, 174,
435/177, 178, 179, 180, 181, 810; 436/503, 518,
528, 529, 536, 537, 543, 547, 808, 501; 260/112
R; 530/389, 810, 813

[56] References Cited

U.S. PATENT DOCUMENTS

| 3,959,078 | 5/1976 | Guire | 435/181 |
| 4,007,089 | 2/1977 | Smith | 435/181 |
| 4,434,150 | 2/1984 | Azad et al. | 435/7 |

OTHER PUBLICATIONS

Guire, "Stepwise Thermophotochemical Crosslinking for Enzyme Stabilization and Immobilization", Enzyme Engineering 3, 63–70, (Plenum Publishing Corporation, 1978).
Friedberg, "Affinity Chromatography and Insoluble Enzymes", Chromatogr. Rev. 14, 121–131 (1971).
Green et al., "The Use of Fifunctional Biotinyl Compounds to Determine the Arrangement of Subunits in Avidin", Biochem J. 125, 781–791 (1971).
Gorman et al., "Transglutaminase Amine Substrates for Photochemical Labelling and Cleavable Cross–Linking of Proteins", J. Biol. Chem. 255, 1175–1180 (1980).
Darfler et al., "Applications of Light–Sensitive Chemicals for Probing Biological Processes", Chap. 2 of *Chemistry and Biochemistry of Amino Acids, Peptides and Proteins*.
Converse et al., Biochem., 8(11): 4431–4436 (1969).
Guire, Methods in Enzymology, VLIV, "Photochemical Immobilization of Enzymes and Other Biochemicals", Academic Press, N.Y., 280–288 (1976).
Chowdhry, Ann. Rev. Biochem., 48: 293–325 (1979).
Erecinska et al., Arch. Biochem. Biophys., 171: 108–116 (1975).
Katzenellenbogen et al., Biochem., 13(14): 2986–2994 (1974).

*Primary Examiner*—Esther M. Kepplinger
*Attorney, Agent, or Firm*—James R. Haller; Mary P. Bauman

[57] ABSTRACT

A method for selectively covalently linking a target moiety to a chemical moiety or carrier comprising attaching to the chemical moiety or carrier a reagent having a selector group capable of forming a specific bond with a receptor carried on the target moiety and attaching a latent reactive group which is capable upon activation of covalently bonding to the target moiety, reacting the selector group with the receptor on the target moiety, and activating the latent group to form a covalent linkage to the target moiety.

13 Claims, No Drawings

4,722,906

BINDING REAGENTS AND METHODS

FIELD OF THE INVENTION

The invention relates to the field of chemistry and particularly to that field in which specific molecular target moieties are to be selectively covalently linked to a chemical moiety or substrate.

BACKGROUND OF THE INVENTION

The isolation of specific molecular moieties is often a necessary step in the process of preparing assay tests for various compounds, particularly in the field of medicine. Such target moieties as enzymes, antibodies and the like are routinely employed in such assays. For example, if a particular chemical moiety such as human growth hormone ("HGH") is to be assayed, the appropriate assay reagent may employ an antibody to the HGH and to which the HGH becomes attached during the assay procedure. Assays of this type are well known to the art, and need not be described further. Reference may be made to Maggio, et al, U.S. Pat. No. 4,233,402, Adams, et al, U.S. Pat. No. 4,039,652 and Murray, et al, U.S. Pat. No. 4,307,071. The antibody and the HGH hence form members of a specific binding pair consisting of the antibody and the hapten fraction of the HGH. Other specific binding pairs are well known and include hormones and hormone receptors, chemical moieties containing specific carbohydrate groups and lectins, and enzymes and their specific binding partners including cofactors, inhibitors and chemical moieties whose reaction the enzymes promote.

Other proposed or current uses of specific binding pair reactions may involve, for example, the uses of antibody-carried poisons or toxins to selectively bind to and kill cancerous cells, and the uses of such reactions in the purification or separation of chemical species.

Although the concept of employing specific binding pairs in various assay procedures and for other uses is well known, it often becomes difficult and hence expensive to select, isolate and bind the specific desired member of the specific binding pair in the preparation of a reagent. The desired binding pair member, commonly a proteinaceous substance such as an antibody, enzyme, etc., often must be selected chemically from a solution containing various other closely related moities. It will be understood that the desired member of a specific binding pair, in many assays of this type, must be bound to other chemical species o to substrates.

DESCRIPTION OF THE PRIOR ART

Guire, U.S. Pat. No. 3,959,078 describes the use of reagents that include both heat-reactive and light-reactive functional groups for the purpose of binding an enzyme to a solid substrate. See also: Guire, *Stepwise Thermophotochemical Crosslinking for Enzyme Stabilization and Immobilization*; Enzyme Engineering 3:63–70 (1976) and Guire, *Photochemical Immobilization of Enzymes and Other Biochemicals*, Methods in Enzymology XLIV:280–288 (1976). Friedberg, *Chromatographic Reviews* 14:121–131 (1971) describes a chromatographic purification system in which an analyte is temporarily coupled to a carrier through members of a specific binding pair carried by each, the analyte thereafter being disassociated from the carrier for subsequent chromatographic analysis. In an article entitled "Affinity Labeling", *Methods in Enzymology*, Vol. XLVI, Academic Press, New York, 1977, there is described a labeling system in which a member of a specific binding pair is provided with a chemically reactive group such that a covalent bond is formed at the epitopic site as a result of the reaction between the specific binding pair. The use of cross-linking reagents containing two identical ligand groups (groups that are members of a specific binding pair) for forming noncovalent cross-links is described in Green, *Bifunctional Reagents and the Quaternary Structure of Proteins.*

SUMMARY OF THE INVENTION

The invention provides methods and compositions for covalently linking to a chemical moiety or substrate a molecular target moiety such as an antibody or enzyme that carries a receptor which is a member of a specific binding pair, preferably without permanently blocking or rendering inactive the receptor site of the target moiety.

In one embodiment, the method of the invention includes the steps of providing the chemical moiety, a carrier which may be, for example, an amino acid such as lysine, aspartic acid, glutamic acid or the like or a solid substrate such as agarose, porous glass or the like, with a selector group that is a member of a specific binding pair and that, as is common with specific binding pairs, is capable of recognizing the receptor and of selectively forming a bond, preferably noncovalent, therewith. The chemical moiety also is provided with a latent reactive group that is capable, upon activation, of covalently bonding to the target moiety, the latent reactive group being sterically distinct from the selector group and desirably permitting the latent reactive group to separate from the selector group by at least about 10 Å.

The method includes the step of contacting the chemical moiety with the target moiety to selectively form a bond between the selector group and the receptor to bring the latent reactive group into covalent bonding proximity with the target moiety, and then activating the latent reactive group to form a covalent bond between the chemical moiety and the target moiety. The bond formed by the reaction between the specific binding pairs is subject to dissociation by various means, preferably after cleavage of the usually fragile bond to the selector group, thereby rendering active the receptor for subsequent reaction in an assay or other procedure.

In another embodiment, a method is provided for selectively attaching a molecular target moiety to a substrate which comprises the steps of attaching to the substrate (a) a selector group forming a member of a specific binding pair of which the other member is a receptor carried by the target moiety, and (b) a latent reactive group capable, upon activation, of covalently bonding to the target moiety when in bonding proximity thereto and sterically distinct and different from the selector group. The method includes the step of reacting the selector group with a receptor carried by the target moiety to bring the latent reactive group into bonding proximity with the target moiety, and then activating the latent reactive group to form a covalent bond between it and the target moiety. Thereafter, the bond formed between the receptor and selector may be dissociated to thereby reactivate the receptor.

In a further embodiment, a method of the invention relates to the attachment of a chemical moiety (including a chemical moiety carried by a substrate) to a selected target moiety in an environment of different chemical species as might exist, for example, in blood serum, the selected target moiety carrying a receptor that is a member of a specific binding pair. The method comprises providing the chemical moiety with a selector group that is the other member of the specific binding pair and that is capable of recognizing the receptor and of bonding thereto. The chemical moiety is provided with a latent reactive group capable, when activated, of forming a covalent bond to the target moiety, the latent reactive group being sterically distinct from, and preferably spacially separable by a distance of at least about 10 Å from, the selector group. The selector group is reacted with the receptor group of the selected target moiety within the environment to position the latent reactive group in bonding proximity with the selected target moiety, and the latent reactive group is then activated to covalently link the latter to the selected target. In this matter, the invention provides a method for readily selecting the desired target moiety from an environment that may contain similar species, and of covalently linking the selected moiety to a desired chemical moiety such as that carried by a substrate. The receptor of the selected target moiety may be reactivated for subsequent use as in an assay procedure or the like.

In yet another embodiment, the invention relates to a reagent for selectively covalently linking a selected proteinaceous or other target moiety to a substrate, the reagent having the general formula

in which:

A represents a latent reactive group capable, in response to specific activation thereof, of covalently bonding to a target moiety in bonding proximity thereto;

B represents a reactive group capable of forming a covalent bond with a substrate, and preferably represents a latent reactive group capable, in response to specific activation to which group A is nonresponsive, of forming said covalent bond;

R represents a selector group that is a member of a specific binding pair and that is reactive to form a bond with a receptor forming the other member of the specific binding pair and that is carried by a selected target moiety; and X represents a relatively inert skeletal radical that is resistant to hydrolysis in aqueous media, that joins groups A, B and R, and that sterically enables group A to be separated from group R by at least 10 Å. Group X desirably is less reactive with group A is the target moiety, and preferably permits to separate from group B by at least about 8 Å.

In yet another embodiment, the invention relates to a chemical reagent for selectively covalently linking a polyvalent radical to a selected target moiety, the reagent having the formula D(A,R) in which:

A represents a latent reactive group capable, in response to activation thereof, of bonding covalently to a target moiety in bonding proximity thereto;

R represents a selector group that is a member of a specific binding pair and that is reactive to form a bond with a receptor forming the other member of the specific binding pair and that is carried by the selected target moiety; and D is a radical, preferably polyvalent, covalently linked to group A and linked to group R and sterically enabling group A to separate from group R by at least about 10 Å. Group D desirably is less reactive with group A than is the target moiety. The reagent D(A,R) may exist as R-D-A, D-R-A or D-A-R, the former being preferred.

DESCRIPTION OF THE PREFERRED EMBODIMENTS

In a preferred embodiment, use is made of a novel reagent which is capable of recognizing and forming a first bond or link to a specific molecular target moiety for the purpose of holding the reagent in covalent bonding proximity with that moiety and of forming a covalent second bond to the target moiety at a site sterically spaced from the first bond. The reagent may carry a different chemical moiety or species to which the target moiety is to be attached, or may itself be attachable to a chemical species that, in turn, may be carried by a solid substrate such as agarose, porous glass, and polystyrene.

In the preferred embodiment, the reagent may have the formula

or D(A,R) in which

A represents a latent reactive group capable, in response to specific activation, of bonding covalently to a target moiety; B represents a reactive group capable, desirably in response to specific activation to which group A is nonresponsive, of forming a covalent bond to a different chemical moiety, such as may be carried by a substrate;

R represents a selector group that is a member of a specific binding pair and that is reactive to form a bond with a receptor forming the other member of the specific binding pair and carried by a selected target moiety;

X represents a relatively inert, non-interfering skeletal radical joining groups "A", "B" and "R" and sterically enabling group A to separate from group "R" by at least about 10 Å; and D is a radical of a selected chemical moiety to be attached to the selected target moiety and, through its chemical links with groups A and R, enables the former to sterically separate from the latter by at least about 10 Å.

Examples of groups typifying group X include amino acids such as cysteine and lysine; aspartic acid, glutamic acid and other dicarboxylic amino acids, and other tri-or poly-functional amino acid derivates.

Examples of groups typifying group D include those listed above, and also enzymes, antibodies or other proteins, polypeptides, water soluble polymers such as polyethylene glycol, dextran, polyvinyl alcohol, polyethylneimine, etc., soluble cellulose polymers, steroids such as hormones, polysaccharides, and the like.

As will now be understood, groups A and R are sterically distinct groups; that is, they may, during the course of thermal vibration and rotation, separate by a distance of at least 10 Å. Group R, a "selector" group, representing a member of a specific binding pair, commonly forms a bond, usually noncovalent, with the target moiety at an epitopic or other binding site of the latter (which site typifies a "receptor" herein). The group A, which upon activation can covalently bond to the target moiety, may be sterically spaced from the group R, thereby enabling the covalent bond to be formed at a site spaced from the receptor site. In turn, the selector-receptor bond may be disassociated from the receptor site through breakage of a fragile bond between the selector group and the chemical moiety followed by removal of the selector by e.g., dialysis, environmental changes (pH, ionic strength, temperature, solvent polarity, etc.) or through spontaneous catalytic modification of the selector group (as when the target moiety is an enzyme), etc. The receptor thus is reactivated to permit subsequent reaction with members of the specific binding pair during an assay or other procedure.

As referred to herein, "specific binding pair" refers to pairs of substances having a specific binding affinity for one another. Such substances include antigens and their antibodies, haptens and their antibodies, enzymes and their binding partners (including cofactors, inhibitors and chemical moieties whose reaction the enzymes promote), hormones and their receptors, specific carbohydrate groups and lectins, vitamins and their receptors, antibiotics and their antibodies and naturally occuring binding proteins, etc. The concept of employing specific binding pairs in analytical chemistry is well known and requires little further explanation. Reference is made to Adams, U.S. Pat. No. 4,039,652, Maggio, et al, U.S. Pat. No. 4,233,402 and Murray, et al, U.S. Pat. No. 4,307,071, the teachings of which are incorporated by reference herein.

The latent reactive group A (and desirably also group B) is a group that, upon suitable activation, covalently bonds to proteinaceous or other target moieties. Such groups are typified by thermochemical groups and photochemical groups, all as described in Guire, U.S. Pat. No. 3,959,078, the teachings of which are incorporated herein by reference. Latent reactive photochemical groups (the covalent bonding of which is activated by actinic radiation) may be typified by aryl, alkyl and acyl azides, oxaziridines, isocyanates (nitrene generators), alkyl and 2-ketodiazo derivatives and diazirines (carbene generators), aromatic ketones (triplet oxygen generators), aromatic diazonium derivatives and numerous classes of carbonium ion and radical generators (Frederick J. Darfler and Andrew M. Tometsko, Ch. 2 of *Chemistry and Biochemistry of Amino Acids, Peptides and Proteins* (Boris Weinstein, Ed) Vol. 5, Marcel Dekker, Inc., New York, 1978). Nitrophenylazide derivatives form a preferred class due to their stability to chemical reaction conditions in the dark and their susceptibility to activation by visible light of wave lengths harmless to most target materials, to form short-lived reactive intermediates capable of forming covalent bonds in useful yield with most sites on the target material. Thermochemical reactive groups (that are activated by heat energy) are typified by and include nitrophenylhalides, alkylamino, alkylcarboxyl, alkylthiol, alkylmethylimidate, alkylisocyanate, alkylisothiocyanate, alkylaldehyde, alkylhalide and other such groups which react with functional groups of support carrier materials.

Inasmuch as enzymes and many other proteinaceous substances that may be employed as target moieties are somewhat sensitive to high temperatures, it is desired that the latent reactive groups employed in the present invention be activated by (that is, covalently bond in response to) easily applied and nonharmful stimuli such as moderate (e.g., body temperature or below) heat, and light. Group A preferably is a photochemical group, and group B preferably is a thermochemical group. Other latent reactive groups may be such groups as react to changes in pH, to the addition of another chemical species, etc. For example, bis (4-fluoro-3-nitrophenyl) sulfone reacts with aminotyrosine residues in proteins (target moiety) at pH 6.5–7.5. This reaction is typical of the great body of common thermochemical reactions that depend upon thermal energy for production of reactive electron configurations. The sulfone reacts also with alkyl amine and phenolic groups at pH 9–10.5. At lower pH, the amine and phenolic groups are protonated and are unreactive with electrophilic reagents. The addition at hydroxyl ion or other acid scavenger typifies the chemical activation of a reactive group. Another example is chemoaffinity labeling with o-phtalaldehyde and (sequentially, in either order) an alkyl amine plus an alkyl thiol to form stable 1-(alkylthio)-2alkylisoindoles (S. Storey Simons, Jr., E. Brad Thompson and David F. Johnson, Biochemistry 18 (1979) 4915). Group X identified above, serves as a skeletal moiety to which the groups A, B and R are linked. It desirably confers some hydrophilic properties to the overall reagent, and performs two important functions. It provides a covalent bonding link between group A and group B, the latter of which may be covalently linked to a chemical moiety as for example may be carried by a solid substrate, and the former of which may be covalently linked to a target moiety. Group X also provides steric distinctness to the groups A and R, preferably enabling such groups to become sterically spaced by at least about 10 Å.

The group D represents a chemical moiety, as may be carried by a solid substrate, and serves to carry the groups A and R sterically distinct from one another in the manner described above.

It will be understood that the chemical bond or link joining the selector group R and the groups D or X need not be a stable or permanent linkage, but rather may be bonds that are readily cleaved without harm to the target moiety; examples include —S—S—, aryldiazo, 3-nitro-4-(aminomethyl)-benzoyloxy, vicinal hydroxyl, bis (methionyl), thioacetal, and bonds susceptable to cleavage by enzymatic catalysis. Reference is made to Gorman et al., J. Biol. Chem 255:1175–1180 (1980).

The invention may be better understood by reference to the following, nonlimiting examples:

EXAMPLE 1

A reagent bound to agarose for the specific immobilization of antibody against the dinitrophenyl (DNP) group was prepared and used with serum from animals immunized with (DNP)-bovine albumin. The commercial reagent chemicals homocysteine thiolactone (HCTL) and diaminodipropylamine (DADPA) were reacted in the presence of oxygen to yield the disulfide, bis-(diaminodipropylamino)-homocystine. This intermediate was immobilized through reaction with a commercially available activated agarose derivative, Reacti-Gel (Pierce Chemical Co.).

The selector derivative, bis-(DNP)-cystamine was prepared through reaction of cystamine with fluoro-2,4-dinitrobenzene, (and is available from commercial sources).

The agarose-DADPA-homocystine was converted to agarose-DADPA-homocysteine through treatment with mercaptoethanol, followed by rinsing with deoxygenated water. The selector group (DNP) was bound to this sulfhydryl-containing carrier derivative through sulfhydryl-disulfide interchange between agarose-DADPAhomocysteine and (DNP)-cystamine, followed by rinsing to produce agarose-DADPA-homocysteine-S-S-cysteine-DNP.

This carrier derivative containing the selector group coupled through a disulfide (—S—S—) bond to the trifunctional homocysteine skeleton, was converted to the photoreactive derivative through reaction with N-(4-azido-3-nitrophenyl)-11-aminoundecanoyl-N-oxy-succinimide ester (ANP-AUD-NOS). This photoaffinity carrier material was prepared, rinsed and stored in the dark or dim light.

Agarose-DADPA-HC=(Cys-DNP, AUD-ANP), as thus prepared, was exposed in dim light to immune serum containing antibodies against DNP in phosphate-buffered saline (PBS) at room temperature overnight. The gel was washed with PBS, followed by illumination for 30-60 minutes with visible light from a slide projector lamp at approximately 4° C.

The selectively immobilized antibody against DNP was tested for DNP binding capacity after washing with mercaptoethanol to break the disulfide bond to the bound DNP-cysteamine, then with pH 2.3 glycine buffer to disassociate the DNP-antibody complex. After washing with PBS, the gel derivative was divided into two portions for comparative measurement of the binding capacity for DNP-glucose oxidase versus native glucose oxidase. The two identical gels containing the different enzyme preparations were packed into a column and eluted with buffer. Assays for glucose oxidase activity content of the washed gels and the washes indicated approximtely 10% of the theoretical DNP-binding capacity (antibody) immobilized by photoaffinity coupling. The specificity of the immobilization was indicated by the failure to immobilize peroxidase activity when horseradish peroxidase was included in the immune serum containing antibody against DNP. Inasmuch as the antibody to the dinitrophenyl group also binds trinitrophenyl group as well, the product of this Example may detect fumes of trinitrotoluene in air or liquids.

EXAMPLE 2

Reacti-Gel (an agarose as reported in Example 1) (1 gram) was taken up in 1 ml. of phosphate buffered saline, and to the resulting suspension was added 10 mg. of lysozyme, a commercial product. The suspension was maintained at pH 9.5 and was gently agitated at room temperature for about 16 hours. Unbound lysozyme was removed by washing with deoxygenated buffered saline, and to the resulting product was added 10 mg. of homocysteine thiolactone, a commercial product. The resulting mixture, maintained under oxygen-free conditions, was agitated at room temperature for an additional 16 hours and was washed with deoxygenated buffer. To the resulting product was then added 10 mg. of (DNP-cysteamine-S-)$_2$, as identified in Example 1. The mixture was agitated gently for 16 hours and then again washed with the phosphate buffered saline. To the resulting product was added, under dim light and gradually over a 16 hour period at room temperature, 10 mg. of the ANP-AUD-NOS product reported in Example 1 dissolved in 0.5 ml. of dimethyl formamide. In the buffer washes reported above, the pH was maintained at about 9.5. The resulting material was washed with a 50% ethanol-phosphate buffered saline solution and then with phosphate buffered saline. The resulting material was added to 1 ml of blood serum from rabbits immunized against dinitrophenyl-bovine albumin. The mixture was incubted overnight at 4° C. and was then subjected to light from a projector lamp for about 60 minutes at 4° C. The resulting material was then packed into columns, and the procedure of Example 1 was repeated. Similar results were obtained.

While a preferred embodiment of the present invention has been described, it should be understood that various changes, adaptations and modifications may be made therein without departing from the spirit of the invention and the scope of the appended claims.

What is claimed is:

1. Method of selectively attaching a molecular target moiety to a carrier, comprising
   (a) attaching to the carrier a reagent having a selector group forming a member of a specific binding pair of which the other member is a receptor carried by the target moiety, and having a latent reactive group that is sterically distinct from the selector group and is capable, upon activation, of covalently bonding to the target moiety;
   (b) reacting th esselector group with the receptor carried by the target moiety to bind the target moiety to the reagent and to bring the latent reactive group into covalent bonding proximity with the target moiety; and
   (c) activating the latent reactiv group to form a covalent linkage to the target moiety.

2. The method of claim 1 including the step of reactivating the receptor for subsequent reaction with nother group that is a member of said specific binding pair.

3. The method of claim 1 in which the latent reactive group is a thermochemical group.

4. A chemical reagent for selectively bonding a molecular target moiety, the reagent having the formula

in which:
   A represents a latent reactive group capable, in response to specific activation thereof, of bonding covalently to the target moiety;
   B represents a reactive group covalently bound to a carrier;
   R represents a selector group that is a member of a specific binding pair and that is reactive to form a bond with a receptor forming the other member of the specific binding pair and that is carried by the target moiety; and
   X represents a skeletal radical joining groups A, B and R and sterically separating group A from group R by at least about 10 Å.

5. The reagent of claim 4 wherein the bond between group R and chemical group X will readily cleave without harm to the target moiety after the target moiety has been covalently bound.

6. Method of attaching a chemical moiety to a selected molecular target moiety in an environment of different chemical species, the selected target moiety carrying a receptor that is a member of a specific binding pair, the method comprising:

(a) providing the chemical moiety with a selector group that is the other member of said specific binding pair and is capable of recognizing the receptor and of bonding thereto;
(b) providing the chemical moiety with a latent active group capable when activated, of forming a covalent bond to the target moiety, the latent reactive group being sterically distinct from the selector group;
(c) reacting the selector group with the receptor of the selected target moiety to position the latent reactive grop in covalently bonding proximity with the selected target moiety;
(d) activating the latent reactive group to form a covalent bond to the selected target moiety; and
(e) reactivating the receptor for subsequent reaction with another group that is a member of said specific binding pair.

7. The method of claim 6 in which the latent reactive group is a photochemical group.

8. The method of claim 6 in which the latent reactive group is a thermochemical group.

9. Method of selectively attaching a molecular target moiety to an insoluble carrier, comprising:
(a) attaching to the carrier a reagent having a selector group forming a member of a specific binding pair of which the other member is a receptor carried by the target moiety, and a latent reactive group that is sterically distinct from the selector group and is capable, upon activation, of covalently bonding to the target moiety;
(b) reacting the selector grop with the receptor carried by the target moiety to bring the latent reactive group into covalent bonding proximity with the target moiety; and
(c) activating the latent reactive group to form a covalent linkage to the target moiety.

10. The method of claim 9 wherein the target moiety is an antibody.

11. The method of claim 9 wherein the latent reactive group is a photochemical group.

12. The method of claim 9 wherein the latent reactive group is a thermochemical group.

13. The method of claim 1 in which the latent reactive group is a photochemical group.

* * * * *

UNITED STATES PATENT AND TRADEMARK OFFICE
CERTIFICATE OF CORRECTION

PATENT NO. : 4,722,906

DATED : February 2, 1988

INVENTOR(S) : Patrick E. Guire

It is certified that error appears in the above—identified patent and that said Letters Patent is hereby corrected as shown below:

Under References Cited: OTHER PUBLICATIONS
Line 7, replace "Fifunctional" with --Bifunctional-- .

Line 18, replace "VLIV" with --XLIV-- .

Column 1, line 49, replace "o" with --or-- .

Column 1, line 58, replace "(1976)" with --(1978)-- .

Column 3, line 56, before "10Å" insert --about-- .

Column 3, line 57, after "A" insert --than-- .

Column 3, line 57, after "permits" insert --Group A-- .

Column 4, lines 60 and 61, replace "polyethylneimine" with -- polyetheyleneimine--.

Column 7, line 7, after "DADPA" insert -- - -- .

Column 8, line 27, after "reacting" replace "th esselector" with --the selector-- .

Column 8, line 33, replace "reactiv" with --reactive-- .

Column 8, line 35, replace "nother" with --another-- .

Column 9, line 5, replace "active" with --reactive-- .

Column 9, line 12, replace "grop" with --group-- .

UNITED STATES PATENT AND TRADEMARK OFFICE
CERTIFICATE OF CORRECTION

PATENT NO. : 4,722,906

DATED : February 2, 1988

INVENTOR(S) : Patrick E. Guire

It is certified that error appears in the above-identified patent and that said Letters Patent is hereby corrected as shown below:

Column 10, line 10, replace "grop" with --group--.

Signed and Sealed this

Third Day of January, 1989

Attest:

DONALD J. QUIGG

*Attesting Officer*  *Commissioner of Patents and Trademarks*